United States Patent [19]

Stubenrauch et al.

[11] Patent Number: 4,496,738
[45] Date of Patent: Jan. 29, 1985

[54] PROCESS FOR PREPARING 1,2,4-TRIAZOLE DERIVATIVES

[75] Inventors: Gerd Stubenrauch; Eberhard Ammermann, both of Ludwigshafen; Gerhard Hamprecht, Weinheim; Ernst-Heinrich Pommer, Limburgerhof, all of Fed. Rep. of Germany

[73] Assignee: BASF Aktiengesellschaft, Fed. Rep. of Germany

[21] Appl. No.: 389,935

[22] Filed: Jun. 18, 1982

Related U.S. Application Data

[63] Continuation of Ser. No. 230,354, Jan. 30, 1981, abandoned, which is a continuation of Ser. No. 83,267, Oct. 10, 1979, abandoned.

[30] Foreign Application Priority Data

Oct. 23, 1978 [DE] Fed. Rep. of Germany ....... 2846038

[51] Int. Cl.$^3$ ................. C07D 249/08; C07D 401/12; C07D 405/12
[52] U.S. Cl. ......................................... 548/262; 546/2; 546/174; 546/175; 546/276; 548/101; 514/938; 534/701; 534/798
[58] Field of Search ............... 548/262, 101; 424/269, 424/245

[56] References Cited

U.S. PATENT DOCUMENTS

| 3,732,242 | 5/1973 | Buchel et al. ............... 548/341 |
| 3,890,442 | 6/1975 | Meiser et al. ............... 424/269 |
| 4,013,677 | 3/1977 | Stelzer et al. ............... 548/262 |
| 4,079,143 | 3/1978 | Balasubramanyan et al. ..... 548/262 |

FOREIGN PATENT DOCUMENTS 2720654 11/1978 Fed. Rep. of Germany ...... 548/262

OTHER PUBLICATIONS

Zoller et al, Tetrahedron, vol. 31, pp. 863–866 (1975).
Chemiakine et al, Mem. Bull. Soc. Chim. France, (1959), pp. 530–533.
Houben-Weyl, Methoden der Organischen Chemie, vol. 6/3, (Stuttgart, 1965), pp. 239–240.
Gross et al, Ber. Deut. Chem. Gesel., vol. 99, pp. 3260–3267 (1966).
Gross et al, Liebig's Ann. Der. Chem., vol. 702, pp. 68–74 (1967).
Gloede et al, J. Prakt. Chem., vol. 311, pp. 497–505 (1969).

Primary Examiner—Alton D. Rollins
Attorney, Agent, or Firm—Keil & Weinkauf

[57] ABSTRACT 1,2,4-Triazole derivatives of the formula

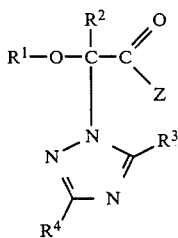

where
$R^1$ is alkyl, alkenyl, alkynyl, cycloalkyl, cycloalkenyl, or unsubstituted or substituted aryl, heteroaryl or arylalkyl,
$R^2$ is hydrogen or, independently of $R^1$, has one of the meanings given for $R^1$,
$R^3$ and $R^4$ independently of one another are each hydrogen, halogen, nitro or lower alkyl and
Z is hydroxyl or a $-O^\ominus M^\oplus$ radical, where $M^\oplus$ is one equivalent of a metal cation or is an unsubstituted or substituted ammonium ion, their preparation, and fungicides containing these compounds.

1 Claim, No Drawings

PROCESS FOR PREPARING 1,2,4-TRIAZOLE DERIVATIVES

This is a continuation, of application Ser. No. 230,354, filed Jan. 30, 1981, which is a continuation of Ser. No. 083,267, filed Oct. 10, 1979, both abandoned.

The present invention relates to novel 1,2,4-triazole compounds, processes for the preparation of these compounds, their use for the preparation of crop protection agents, dyes and/or drugs, and fungicides containing the said triazole derivatives.

It is known that O,N-acetals of α-ketocarboxylic acids are obtained when (a) dichloroacetic acid is converted, with an alcoholate, into a symmetrical glyoxylic acid O,O-acetal (cf. Houben-Weyl, "Methoden der organischen Chemie", Volume 6/3, pages 239/240, G. Thieme-Verlag, Stuttgart 1965), the latter is then reacted with an acid halide to give a 2-halo-2-alkoxyacetic acid derivative (cf. Chem. Ber. 99 (1966), 3260 et seq.) and this is reacted with an amine to give the desired glyoxylic acid O,N-acetal (cf. Liebigs Ann. Chem. 702 (1967), 68 et seq.), or (b) a dichloroacetic acid ester is first reacted with an amine to give the symmetrical N,N-acetal of the corresponding glyoxylic acid amide (cf. Liebigs Ann. Chem. 702 (1967), 70), the latter is converted to the symmetrical N,N-acylal and this is reacted with an alcohol to give the N-acylated N,O-acetal of the corresponding glyoxylic acid amide (cf. J. prakt. Chem. 311 (1969), 497 et seq.), or (c) glyoxylic acid is reacted with an acid amide to give a 2-N-acylamino-2-hydroxyacetic acid and the latter is converted with alcoholic sulfuric acid into the N-acylated N,O-acetal of the corresponding glyoxylic acid ester (cf. Tetrahedron 31 (1975), 863 et seq.) or (d) an aminoacid is dehydrated to an oxazol-5-one, the latter is halogenated to give the 4-halooxazol-5-one and this compound is converted, by ring cleavage and alcoholysis, to the desired N-acylated N,O-acetal of the corresponding α-ketocarboxylic acid ester (cf. Mem. Bull. Soc. Chim. France 1959 530 et seq.).

These processes have the disadvantage that several reaction steps are always necessary to arrive at the end product, so that the final yields, based on starting materials, are very low. Further, the range of applicability of these methods is narrow; for example, O-aryl-α-ketocarboxylic acid O,N-acetals cannot be prepared by these methods.

The process of the present invention, described below, now offers a surprisingly simple way of arriving at novel α-ketocarboxylic acid O,N-acetals. The compounds according to the invention themselves exhibit good fungicidal effects and in addition are valuable intermediates for the preparation of crop protection agents, dyes and drugs.

The invention relates to compounds of the general formula I

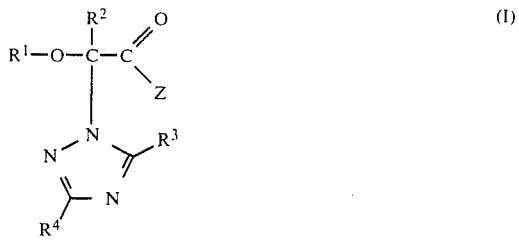

where
$R^1$ is alkyl, alkenyl, alkynyl, cycloalkyl, cycloalkenyl, or unsubstituted or substituted aryl, heteroaryl or aryalkyl,
$R^2$ is hydrogen or, independently of $R^1$, has one of the meanings given for $R^1$,
$R^3$ and $R^4$ independently of one another are each hydrogen, halogen, nitro or lower alkyl and
Z is hydroxyl or a $-O^\ominus M^\oplus$ radical, where $M^\oplus$ is one equivalent of a metal cation or is an unsubstituted or substituted ammonium ion.

In the formula I, $R^1$ is preferably straight-chain alkyl of 1 to 6, especially of 1 to 4, carbon atoms, or branched alkyl of 3 to 7, especially of 3 to 5, carbon atoms, e.g. methyl, ethyl, n-propyl, i-propyl, n-butyl, sec.-butyl, tert.-butyl, amyl or hexyl; straight-chain alkenyl of 2 to 6, especially of 3 to 6, carbon atoms, or branched alkenyl of 3 to 7, especially of 3 to 6, carbon atoms, e.g. allyl, methallyl, crotyl, 2-methylbut-2-en-1-yl, 3-methylbut-1-en-3-yl or hex-2-en-1-yl; straight-chain alkynyl of 2 to 6, especially of 3 to 6, carbon atoms, or branched alkynyl of 3 to 7, especially of 3 to 6, carbon atoms, e.g. propargyl, but-2-yn-1-yl, but-1-yn-3-yl or 3-methyl-but-1-yn-3-yl; unsubstituted or alkyl-substituted cycloalkyl of 3 to 7, especially of 3 to 6, carbon atoms in the ring, e.g. cyclopropyl, methylcyclopentyl or dimethylcyclohexyl; unsubstituted or alkyl-substituted cycloalkenyl of 4 to 7, especially of 5 to 6, carbon atoms in the ring, e.g. cyclopent-2-en-1-yl or 3-methylcyclohex-2-en-1-yl; unsubstituted or substituted heteroaryl of 5 to 7, especially of 5 or 6, ring atoms, of which 1, 2 or 3, especially 1 or 2, are heteroatoms, which may be identical or different and are preferably oxygen, sulfur or nitrogen, e.g. unsubstituted or substituted pyridyl, pyrazolyl or pyrimidinyl; unsubstituted or substituted aryl of 6 to 20 carbon atoms, especially unsubstituted or substituted phenyl, naphthyl, tolyl or xylyl; or unsubstituted or substituted aralkyl of 6 to 10 carbon atoms in the aryl part and 1 or 2 carbon atoms in the alkyl part, in particular unsubstituted or substituted benzyl or α-phenylethyl. Preferred substituents of the aryl, heteroaryl and arylalkyl radicals are halogen, especially fluorine, chlorine, or bromine; nitro; straight-chain alkyl of 1 to 14, especially of 1 to 12, carbon atoms; branched alkyl of 3 to 14, especially of 3 to 12, carbon atoms, alkylthio of 1 to 4, especially of 1 to 3, carbon atoms; haloalkyl of 1 to 4, especially of 1 to 3, carbon atoms and 1 to 9 halogen atoms, halogen being, in particular, fluorine or chlorine; haloalkylthio, haloalkoxy or haloalkylsulfonyl of 1 to 3 carbon atoms and 1 to 7 halogen atoms; cyano, thiocyanato, formyl, alkoxycarbonyl, dialkylketonyl, alkylcarbonyl, alkylcarbamyl, dialkylcarbamyl, acylamino, or alkylaminosulfonyl of 2 to 12, especially of 2 to 10, carbon atoms, e.g. methoxycarbonyl, acetonyl, propionyl, N,N-dimethylcarbamyl or butyrylamino; alkoxyalkyl or alkylthioalkyl of 1 to 8, especially of 1 to 6, carbon atoms, e.g. ethoxypropyl or methylmercaptomethyl; unsubstituted or substituted phenyl of 6 to 11 carbon atoms or phenylcarbonyl of 7 to 11 carbon atoms; unsubstituted or substituted aryloxy, in particular in the 4-position, e.g. 4-(4′-chlorophenoxy), 4-(2′4′-dichlorophenoxy) or 4-(4′-trifluoromethylphenoxy); unsubstituted or substituted phenylazo, especially in the 4-position e.g. 4-(4′-chlorophenylazo) or 4-(3′-fluorophenylazo); unsubstituted or substituted arylthio, arylsulfinyl or arylsulfonyl; unsubstituted or substituted aralkyl, especially substituted or unsubstituted benzyl or benzyloxy; straight-chain alkenyl of 2 to 6, especially of 2 to 4, carbon atoms; branched alkenyl of 3 to 7, especially of 3 to 6, carbon atoms; straight-chain alkynyl of 2 to 6, especially of 2 to 4, carbon atoms; branched alkynyl of 3 to 7, especially of 3 to 6, carbon atoms, or a fused ring, especially from the group of the aromatics and heterocyclics, e.g. unsubstituted or substituted benzo, benzofuro or pyridino.

$R^2$ is preferably hydrogen, straight-chain alkyl of 1 to 10, especially 1 to 6, carbon atoms, branched alkyl of 3 to 8, especially 3 to 6, carbon atoms, cycloalkyl of 3 to 7, especially of 3 to 6, carbon atoms in the ring, unsubstituted or substituted aryl of 6 to 12 carbon atoms, or unsubstituted or substituted arylalkyl of 6 to 12 carbon atoms in the aryl part and 1 to 2 carbon atoms in the alkyl part. A particularly preferred class of triazole derivatives of the general formula I, to which class the invention is however in no way restricted, is where $R^1$ is aryl or heteroaryl which may or may not be substituted or fused as described above, $R^2$ is hydrogen, straight-chain $C_{1-4}$-alkyl, branched $C_{3-4}$-alkyl or unsubstitued or substituted phenyl or benzyl, $R^3$ and $R^4$ are hydrogen, methyl or ethyl and Z is OH.

The compounds of the formula I have one or more chiral centers; pure isomers can be obtained from the mixtures, obtained by synthesis, in accordance with prior art methods.

Compounds of the formula I may also be in the form of zwitterions and we also claim the compounds in this form.

The invention further relates to a process for the preparation of a compound of the general formula I, wherein a compound of the general formula II

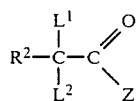
(II)

where $R^2$ and Z have the above meanings and $L^1$ and $L^2$ are nucleophilically displaceable leaving groups, is reacted with a hydroxy compound of the general formula III

 (III)

where $R^1$ has the above meaning, and a 1,2,4-triazole of the general formula IV

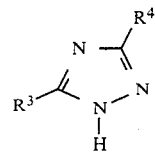
(IV)

where $r^3$ and $R^4$ have the above meanings, in the presence or absence of a solvent or diluent and/or of an acid acceptor and in the presence or absence of a reaction accelerator at from 0° to 180° C.

Suitable nucleophilically displaceable leaving groups are in particular halogen, bisulfate, halosulfonate, unsubstituted or substituted arylsulfonyloxy, alkylsulfonyloxy, alkylsulfate, oxonium, sulfonium or ammonium radicals.

Instead of the free hydrogen compounds of the formulae I and IV it is also possible to employ corresponding salts, for example alkali metal salts, alkaline earth metal salts or unsubstituted or substituted ammonium salts, which are produced by conventional methods in a preliminary reaction or, where appropriate, in situ by adding an equivalent amount of an organic or inorganic base.

If phenol, 1,2,4-triazole and dichloroacetic acid are used as starting materials, the course of the reaction in the process according to the invention may be represented by the following equation:

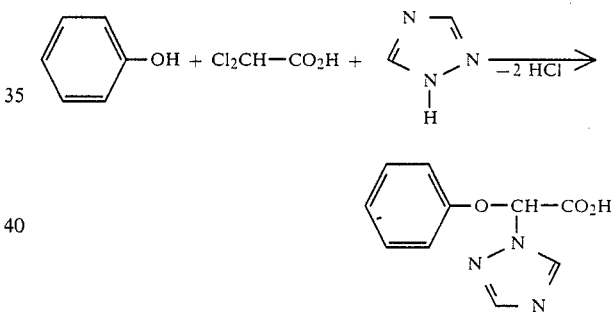

The preferred solvents or diluents include polar solvents, e.g. water; formamides, e.g. dimethylformamide, formamide and dimethylacetamide; nitriles, e.g. acetonitrile, benzonitrile and butyronitrile; sulfoxides, e.g. dimethylsulfoxide; phosphoric acid amides, e.g. hexamethylphosphorotriamide; ketones, e.g. acetone, ethyl methyl ketone, cyclohexanone and acetophenone; ethers, e.g. tetrahydrofuran, anisole, dimethoxyethane, n-butyl ethyl ether and dioxane; nitroalkanes, e.g. nitromethane; nitrobenzene; alcohols, e.g. methanol, ethanol, isopropanol, n-butanol and 3-methylbutanol; ureas, e.g. tetramethylurea; ether-alcohols, e.g. ethylene glycol monomethyl ether; sulfones, e.g. sulfolane; and esters, e.g. ethyl acetate, methyl propionate and methyl formate. However, it is also possible to use halohydrocarbons, especially chlorohydrocarbons, e.g. methylene chloride, chloroform, 1,2-dichloroethane, 1,1,2,2- or 1,1,1,2-tetrachloroethane, dichloropropane, trichloroethylene, chlorobenzene, o-, m- or p-dichlorobenzene, fluorobenzene, o-, m- or p-chlorotoluene, dichloronaphthalene and carbon tetrachloride; aliphatic or cycloaliphatic hydrocarbons, e.g. heptane, pinane, o-, m- and p-cymene, gasoline fractions within a boiling range of from 70° to 190° C., cyclohexane, methylcyclohexane, decalin, petroleum ether, naphtha, 2,2,4-trimethylpentane and octane; aromatic hydrocarbons, e.g. benzene, toluene, o-, m- or p-xylene and tetralin, and mixtures of the above. Advantageously the solvent is used in an amount of from 100 to 2,000% by weight, preferably from 100 to 1,000% by weight, based on the starting material of the formula III or IV.

The process according to the invention is preferably carried out in the presence of an organic or inorganic base. In particular, basic hydroxy compounds, basic oxides, tertiary amines, alcoholates, carbonates or hydrides are used, e.g. potassium hydroxide, sodium hydroxide, potassium carbonate, calcium hydroxide, calcium oxide, barium oxide, magnesium hydroxide, magnesium oxide, barium hydroxide, calcium carbonate, magnesium carbonate, magnesium bicarbonate, zinc hydroxide, zinc oxide, zinc carbonate, zinc bicarbonate, sodium methylate, magnesium ethylate, potassium ethylate, sodium propylate, aluminum isopropylate, sodium butylate, lithium methylate, potassium cyclohexanolate, sodium isopropylate, potassium tert.-butylate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-diisopropylaniline, N,N-dimethyltoluidine, N,N-diethyltoluidine, N,N-dipropyltoluidine, N,N-dimethyl-p-amino-pyridine, N,N-diethyl-p-aminopyridine, N-methylpiperidine, N-ethylpiperidine, N-methylpyrrolidine, N-ethylpyrrolidine, N-methylpyrrole, N-methylmorpholine, N-ethylmorpholine, N-methylhexamethyleneimine, pyridine, quinoline, α-, β-and γ-picoline, N,N,N',N'-tetramethylethylethylenediamine, N-ethyldiisopropylamine, N,N-dimethylcyclohexylamine, sodium hydride, lithium hydride and calcium hydride. However, other basic compounds usually employed are also suitable.

Preferred reaction accelerators are metal iodides and bromides, e.g. sodium iodide, potassium bromide and calcium iodide, crown ethers, quaternary ammonium compounds, e.g. tetrabutylammonium iodide or bromide, acids or combinations of these compounds.

The process according to the invention is in general carried out at from 0° to 180° C., preferably from 40° to 100° C., for from 30 minutes to 120 hours, preferably from 1 hour to 60 hours, under atmospheric or superatmospheric pressure, continuously or batchwise. In carrying out the process according to the invention, the amounts employed per mole of compound II are in general from 0.5 to 2 moles of compound III and 0.5 to 2 moles of triazole IV, preferably from 0.9 to 1.2 moles of compound III and from 0.9 to 1.4 moles of triazole IV, as well as from 3 to 6 moles, preferably from 2.8 to 3.3 moles, of base, with or without from 0.01 to 0.1 mole of the reaction accelerator.

In a preferred form of the process according to the invention, the starting materials III and IV are mixed, in optional sequence, with a base and an organic diluent or water, the starting material II, with or without a reaction accelerator, is then added and the reaction is carried out at from 0° to 180° C., preferably from 40° to 110° C., for from 0.5 to 120, preferably from 1 to 60, hours. To isolate the compounds according to the invention, where water or a water-miscible organic diluent has been used, the reaction mixture— with or without prior concentration, is poured onto ice water, and mineral acid is added, whilst cooling with ice, until a strongly acid reaction is obtained. Any unreacted triazole is thereby removed and the reaction product which has precipitated is filtered off, washed to remove any starting material III which may still be adhering to it, and dried; in general, the product does not require any further purification, but if necessary it can be additionally purified by conventional methods, such as recrystallization, extraction and chromatography. In the case of water-immiscible solvents the reaction batch is poured into water, the phases are separated, the organic phase is extracted, if necessary, with aqueous alkali or saturated bicarbonate solution, and the desired end product is isolated by acidifying the aqueous alkaline phase as described above.

EXAMPLE 1

90 parts of a technical-grade sodium methylate solution in methanol (30 parts of sodium methylate in 100 parts of solution) are added to 81.5 parts of 2,4-dichlorophenol and 34.5 parts of 1,2,4-triazole in 300 parts of ethanol and after brief stirring 109 parts of dibromoacetic acid are introduced. The mixture is refluxed for 14 hours, the solvent is stripped off and the residue is dissolved in about 1,000 parts of water. Ice is added, the pH is brought to 1 by adding concentrated hydrochloric acid whilst stirring, and the precipitate which has formed is filtered off and washed with isopropanol. After drying, 121 parts (84% of theory) of 2-(2',4'-dichlorophenoxy)-2-(1',2',4'-triazol-1'-yl)-acetic acid, of melting point 211°–213° C. (with decomposition), are obtained.

EXAMPLE 2

771 parts of 4-chlorophenol and 414 parts of 1,2,4-triazole are added to 1,080 parts of a technical-grade sodium methylate solution in methanol (30 parts of sodium methylate in 100 parts of solution). After briefly stirring the mixture, 774 parts of dichloroacetic acid are run in, during which addition the temperature rises to about 60° C. The methanol is then distilled off and isopropanol is run in at the same time in such amount that the reaction mixture can be stirred without difficulty. When the internal temperature has reached 80° C., boiling is continued for 10 hours, the solvent is then distilled off, ice water is added and the mixture is acidified with concentrated hydrochloric acid. The precipitate formed is filtered off, washed with isopropanol and dried. 676 parts (58% of theory) of 2-(4'-chlorophenoxy)-2-(1', 2',4'-triazol-1'-yl)-acetic acid of melting point 205°–207° C. (with decomposition) are obtained.

EXAMPLE 3

94 parts of phenol and 70 parts of 1,2,4-triazole are added to a solution of 23 parts of sodium in 600 parts of isopropanol. 129 parts of dichloroacetic acid and 1 part of sodium iodide are then added and the reaction mixture is refluxed for 5 hours. The solvent is then stripped off, the residue is dissolved in water and the solution is acidified with concentrated hydrochloric acid. The precipitate formed is filtered off, washed with diisopropyl ether and dried. This gives 142 parts (66% of theory) of 2-phenoxy-2-(1',2',4'-triazol-1'-yl)-acetic acid of melting point 180°–183° C. (with decomposition).

The following compounds of the formula I, for example, may be prepared similarly.

TABLE

| Example No. | R¹ | R² | Z | R³ | R⁴ | Melting point [°C.] |
|---|---|---|---|---|---|---|
| 4 | 2-Cl, 4-Br-phenyl | H | OH | H | H | 209–213 (decomposition) |
| 5 | 2-CH₃, 4-Cl-phenyl | H | OH | H | H | 178–181 (decomposition) |
| 6 | naphth-1-yl | H | OH | H | H | 210–216 (decomposition) |
| 7 | naphth-2-yl | H | OH | H | H | 197–199 (decomposition) |
| 8 | 4-(benzyl)phenyl | CH₃ | OH | H | H | |
| 9 | 4-Cl-phenyl | CH₃ | OH | H | H | 148–152 |
| 10 | 2,4,5-trichlorophenyl | H | OH | H | H | 218–223 (decomposition) |
| 11 | 4-(phenylsulfonyl)phenyl | H | OH | H | H | |
| 12 | 4-phenoxyphenyl | H | OH | H | H | |
| 13 | 4-(4-chlorophenoxy)phenyl | H | OH | H | H | |
| 14 | 2,4-dichloro-6-phenoxyphenyl | H | OH | H | H | 127–130 (decomposition) |
| 15 | 4-CH₃O-phenyl | H | OH | H | H | 174–175 |

| Example No. | R¹ | R² | Z | R³ | R⁴ | Melting point [°C.] |
|---|---|---|---|---|---|---|
| 16 | C₆H₅–CH₂O–C₆H₄– | H | OH | H | H | 195–198 |
| 17 | 2,4-Cl₂–C₆H₃– | H | ON(C₂H₅)₃ (with H) | H | H | Oil |
| 18 | 3-pyridyl | H | OH | H | H |  |
| 19 | 4-F–C₆H₄–N=N–C₆H₄– | H | OH | H | H | 233–238 |
| 20 | 3,4-F₂–C₆H₃–N=N–C₆H₄– | H | OH | H | H | 225 (decomposition) |
| 21 | 3-F–C₆H₄–N=N–C₆H₄– | H | OH | H | H | 225 (decomposition) |
| 22 | C₆H₅–CH₂–C₆H₄– | C₆H₅ | OH | H | H |  |
| 23 | C₆H₅–C₆H₄– (biphenyl) | CH₃ | OH | H | H | 150–153 |
| 24 | C₆H₅–C₆H₄– (biphenyl) | H | OH | CH₃ | CH₃ |  |
| 25 | 4-CF₃–C₆H₄–O–C₆H₄– | H | OH | H | H |  |
| 26 | C₆H₅–CO–C₆H₄– | H | OH | H | H | 207–211 |
| 27 | 8-quinolyl | H | OH | H | H |  |

TABLE-continued

| Example No. | R¹ | R² | Z | R³ | R⁴ | Melting point [°C.] |
|---|---|---|---|---|---|---|
| 28 | 2,4-dichlorophenyl | H | H, ON(C₄H₉)₃ | H | H | |
| 29 | 2-biphenylyl | H | OH | H | H | 143–147 |
| 30 | 2-isopropylphenyl | H | OH | H | H | |
| 31 | 4-(1-phenylethyl)phenyl | H | OH | H | H | |
| 32 | 4-(phenylsulfinyl)phenyl | H | OH | H | H | |
| 33 | 3-(trifluoromethyl)phenyl | H | OH | H | H | 172–177 |
| 34 | 3-fluorophenyl | H | OH | H | H | 169–176 (decomposition) |
| 35 | 4-fluorophenyl | H | OH | H | H | 174–176 |
| 36 | 4-fluorophenyl | H | OH | CH₃ | H | |
| 37 | 3-pyridyl | H | OH | H | H | |
| 38 | 4-benzylphenyl | H | OH | H | H | 175–178 (decomposition) |

TABLE-continued

| Example No. | R¹ | R² | Z | R³ | R⁴ | Melting point [°C.] |
|---|---|---|---|---|---|---|
| 39 | 3-nitrophenyl | H | OH | H | H | 122–123 |
| 40 | biphenyl-4-yl | H | OH | H | H | 222–224 |
| 41 | 7,8-dichlorodibenzofuran-2-yl | H | OH | H | H | |
| 42 | dibenzofuran-2-yl | H | OH | H | H | |
| 43 | 2,4-dimethylphenyl | H | OH | H | H | 177–179 (decomposition) |
| 44 | 4-(phenylsulfonyl)phenyl | H | OH | H | H | |
| 45 | biphenyl-4-yl | H | ON(C₂H₅)₃ with H | H | H | |
| 46 | biphenyl-4-yl | H | OH | H | CH₃ | |
| 47 | 4-tert-butylphenyl | H | OH | H | H | 198–200 |
| 48 | 4-tert-butylphenyl | CH₃ | OH | H | H | 152–155 |
| 49 | (halo)phenyl | H | OH | H | H | 142–150 |
| 50 | phenyl | phenyl | OH | H | H | |

TABLE-continued

| Example No. | R¹ | R² | Z | R³ | R⁴ | Melting point [°C.] |
|---|---|---|---|---|---|---|
| 51 | 4-cyclohexylphenyl | H | OH | H | H | 195–201 |
| 52 | 4-biphenylyl | phenyl | OH | H | H |  |
| 53 | 4-(n-C₈H₁₇)-phenyl | H | OH | H | H |  |
| 54 | 4-(2-phenylpropan-2-yl)phenyl | H | OH | H | H |  |
| 55 | 3-chloro-4-biphenylyl | H | OH | H | H | 194–198 (decomposition) |
| 56 | 4-(n-C₉H₁₉)-phenyl | H | OH | H | H |  |
| 57 | 4-chlorophenyl | phenyl | OH | H | H |  |
| 58 | 4-(diphenylmethyl)phenyl | H | OH | H | H |  |
| 59 | CH₃ | H | OH | H | H |  |
| 60 | CH₃ | CH₃ | OH | H | H |  |
| 61 | C₂H₅ | H | OH | H | H |  |
| 62 | tert.-C₄H₉ | H | OH | H | H |  |
| 63 | benzyl (C₆H₅CH₂) | H | OH | H | H |  |
| 64 | 2,4-dichlorobenzyl | H | OH | H | H |  |
| 65 | 4-(phenylthio)phenyl | H | OH | H | H |  |

TABLE-continued

| Example No. | R¹ | R² | Z | R³ | R⁴ | Melting point [°C.] |
|---|---|---|---|---|---|---|
| 66 | 2,6-dimethylphenyl (H₃C, CH₃, CH₃ substituted phenyl) | H | OH | H | H | 170–174 (decomposition) |
| 67 | (C₆H₅)₂CH–OCH₃ (methoxydiphenylmethyl) | H | OH | H | H | |
| 68 | 4-chlorobiphenyl (Cl-C₆H₄-C₆H₄-) | H | OH | H | H | |
| 69 | 3,4-dichlorophenyl | H | ONH₃tert.-C₄H₉ | H | H | 156–158 |
| 70 | 2-biphenylyl substituted | H | OH | H | H | 125–137 (decomposition) |

The compounds according to the invention and their metal complexes exhibit an excellent action against a broad spectrum of phytopathogenic fungi, especially from the class of the Ascomycetes and Basidiomycetes. Some of them have a systemic action and can be employed as leaf fungicides and soil fungicides.

The fungicidal compounds are of particular interest for combating a plurality of fungi on various crop plants or their seed.

For the purposes of this invention, crop plants in particular include wheat, rye, barley, oats, rice, Indian corn, cotton, soybean, coffee, sugar cane, fruit and ornamental plants in horticulture, as well as vegetables such as beans, cucumbers and other Cucurbitaceae.

The novel compounds are particularly suitable for combating the following plant diseases: *Erysiphe graminis* (powdery mildew) in cereals, *Erysiphe cichoriacearum* (powdery mildew) in Cucurbitaceae, *Podosphaera leucotricha* in apples, *Uncinula necator* in vines, *Erysiphe polygoni* in beans, *Sphaerotheca pannosa* in roses, species of Puccinia in cereals, *Rhizoctonia solani* in cotton, species of Helminthosphorium in cereals, species of Ustilago in cereals and sugar cane, *Rhynchosporium secale* in cereals, and *Venturia inaequalis* (apple scab).

The compounds are used by spraying or atomizing the active ingredients onto the plants or dressing the plant seeds with the active ingredients. They may be used before or after infection of the plants or seed by the fungi.

The compounds according to the invention can be converted to the conventional formulations, e.g. solutions, emulsions, suspensions, dusts, powders, pastes and granules. The form in which they are used depends entirely on the particular objective; however, it should in every case ensure fine and uniform distribution of the active ingredient. The formulations are prepared in the conventional manner, for example by extending the active ingredient with a solvent and/or carrier, with or without addition of an emulsifier or dispersant and, where water is used as the diluent, with or without addition of an organic auxiliary solvent. Essentially, the following may be used as such auxiliary ingredients: solvents, such as aromatics (e.g. xylene or benzene), chloroaromatics (e.g. chlorobenzenes), paraffins (e.g. petroleum fractions), alcohols (e.g. methanol or butanol), amines (e.g. ethanolamine), dimethylformamide and water; carriers, such as natural rock powders (e.g. kaolins, aluminas, talc or chalk) and synthetic rock powders (e.g. highly disperse silica and silicate); emulsifiers, such as non-ionic and anionic emulsifiers (e.g. polyoxyethylene fatty alcohol ethers, alkylsulfonates and arylsulfonates); and dispersants, such as lignin, sulfite waste liquors and methylcellulose.

The fungicidal formulations in general contain from 0.1 to 95% by weight of active ingredient, preferably from 0.5 to 90%.

The amounts applied are from 0.01 to 3, but preferably from 0.01 to 1, kg of active ingredient per hectare, depending on the nature of the desired effect.

The fungicides and the finished formulations prepared therefrom, e.g. solutions, emulsions, suspensions, powders, dusts, pastes or granules, are applied in the conventional manner, for example by spraying, atomizing, dusting, scattering, dressing or watering.

Examples of such formulations are:

I. 90 parts by weight of the compound of Example 1 are mixed with 10 parts by weight of N-methyl-α-pyrrolidone and a solution suitable for use in the form of very fine droplets is obtained.

II. 20 parts by weight of the compound of Example 4 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of calcium dodecylbenzenesulfonate and 5 parts by weight of the adduct of 40 moles of ethylene oxide with 1 mole of castor oil. On pouring this solution into 100,000 parts by weight of water, and finely dispersing it therein, an aqueous dispersion containing 0.02% by weight of active ingredient is obtained.

III. 20 parts by weight of the compound of Example 16 are dissolved in a mixture consisting of 40 parts by weight of cyclohexanone, 30 parts by weight of isobutanol, and 20 parts by weight of the adduct of 40 moles of ethylene oxide with 1 mole of castor oil. On pouring this solution into 100,000 parts by weight of water, and dispersing it therein, an aqueous dispersion containing 0.02% by weight of active ingredient is obtained.

IV. 20 parts by weight of the compound of Example 19 are dissolved in a mixture which consists of 25 parts by weight of cyclohexanol, 65 parts by weight of a mineral oil fraction of boiling point 210°–280° C. and 10 parts by weight of the adduct of 40 moles of ethylene oxide with 1 mole of castor oil. On pouring this solution into 100,000 parts by weight of water, and finely dispersing it therein, an aqueous dispersion containing 0.02% by weight of active ingredient is obtained.

V. 20 parts by weight of the compound of Example 21 are thoroughly mixed with 3 parts by weight of sodium diisobutylnaphthalene-α-sulfonate, 17 parts by weight of the sodium salt of a ligninsulfonic acid obtained from a sulfite waste liquor and 60 parts by weight of silica gel powder, and the mixture is milled in a hammer mill. On finely dispersing the mixture in 20,000 parts by weight of water, a spray liquor containing 0.1% of active ingredient is obtained.

VI. 3 parts by weight of the compound of Example 26 are intimately mixed with 97 parts by weight of finely divided kaolin. A dusting agent containing 3% by weight of active ingredient is thus obtained.

VII. 30 parts by weight of the compound of Example 43 are intimately mixed with a mixture of 92 parts by weight of silica gel powder and 8 parts by weight of paraffin oil which has been sprayed onto the surface of the silica gel. A formulation of the active ingredient which clings well is thus obtained.

VIII. 40 parts by weight of the compound of Example 49 are intimately mixed with 10 parts by weight of the sodium salt of a phenolsulfonic acid/urea/formaldehyde condensate, 2 parts by weight of silica gel and 48 parts by weight of water. A stable aqueous dispersion is obtained. On dilution with 100,000 parts by weight of water, an aqueous dispersion containing 0.04% by weight of active ingredient is obtained.

IX. 20 parts of the compound of Example 55 are intimately mixed with 2 parts of calcium dodecylbenzenesulfonate, 8 parts of a fatty alcohol polyglycol ether, 2 parts of the sodium salt of a phenolsulfonic acid/urea/formaldehyde condensate and 68 parts of a paraffinic mineral oil. A stable oily dispersion is obtained.

In the forms for use described above, the agents according to the invention can also be accompanied by other active ingredients, for example herbicides, insecticides, growth regulators and other fungicides, or be mixed with fertilizers, and applied as such mixtures. When mixed with other fungicides, a broader fungicidal action spectrum is often achieved.

The list of fungicides given below, with which the compounds according to the invention can be combined, is intended to illustrate the scope for combinations, without implying any limitation.

Accordingly, examples of fungicides which may be combined with the compounds according to the invention are: dithiocarbamates and their derivatives, eg. iron (III) dimethyldithiocarbamate, zinc dimethyldithiocarbamate, manganese ethylene-bis-dithiocarbamate, manganese-zinc ethylenediamine-bis-dithiocarbamate, zinc ethylene-bis-dithiocarbamate, tetramethylthiuram disulfides, the ammonia complex of zinc N,N-ethtylene-bis-dithiocarbamate and N,N'-polyethylene-bis-(thiocarbamyl)-disulfide, zinc N,N'-propylene-bis-dithiocarbamate, the ammonia complex of zinc N,N'-propylene-bis-dithiocarbamate and N,N'-polypropylene-bis-(thiocarbamyl)-disulfide; nitro derivatives, eg. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic structures, eg. N-trichloromethylthio-tetrahydrophthalimide, N-trichloromethylthio-phthalimide, 2-heptadecyl-2-imidazoline-acetate, 2,4-dichloro-6-(o-chloroanilino)-s-triazine, 0,0-diethyl-phthalimidophosphonothioate, 5-amino-1-(bis-(dimethylamino)-phosphinyl)-3-phenyl-1,2,4 -triazole, 5-ethoxy-3-trichloromethyl-1,2,4-thiadiazole, 2,3-dicyano-1,4-dithioanthraquinone, 2-thio-1,3-dithio-(4,5-b)-quinoxaline, 1(butylcarbamyl)-2-benzimidazole-carbamic acid methyl ester, 2-methoxycarbonylamino-benzimidazole, 2-thiocyanatomethylthio-benzthiazole, 4(2-chlorophenylhydrazono)-3-methyl-isoxazol-5-one, pyridine-2-thiol-1-oxide, 8-hydroxyquinoline and its copper salt, 2,3-dihydro-5-carboxanilido-6-methyl-1,4-oxathiine-4,4-dioxide, 2,3-dihydro-5-carboxanilido-6-methyl-1,4-oxathiine, 2-(fur-2-yl)-benzimidazole, piperazine-1,4-diyl-bis-(1-(2,2,2-trichloro-ethyl)-formamide), 2-(thiazol-4-yl)-benzimidazole, 5-butyl-2-dimethylamino-4-hydroxy-6-methyl-pyrimidine, bis-(4-chlorophenyl)-3-pyridinemethanol, 1,2-bis-(3-ethoxycarbonyl-2-thioureido)-benzene and 1,2-bis-(3-methoxycarbonyl-2-thioureido)-benzene, and various fungicides such as dodecylguanidine acetate, 3-(2-(3,5-dimethyl-2-oxocyclohexyl)-2-hydroxyethyl)-glutarmide, hexachlorobenzene, N-dichlorofluoromethylthio-N',N'-dimethyl-N-phenyl sulfuric acid diamide, 2,5-dimethyl-furan-3-carboxylic acid anilide, 2,5-dimethyl-furan-3-carboxylic acid cyclohexylamide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, DL-methyl-N-(2,6-dimethyl-phenyl)-N-furo-2-yl-alaninate, DL-N-(2,6-dimethyl-phenyl)-N-(2'-methoxyacetyl)-alanine methyl ester, diisopropyl 5-nitro-isophthalate, 1-(1',2',4'-triazol-1'-yl)-[1-(4'-chlorophenoxy)]-3,3-dimethyl-butan-2-one, 1-(1',2',4'-triazol-1'-yl)-8 1-(4'-chlorophenoxy)]-3,3-dimethyl-butan-2-ol, N-(2,6-dimethylphenyl)-N-chloroacetyl-D,L-2-aminotbutyrolactone and N-(n-propyl)-N-(2,4,6-trichlorophenoxyethyl)-N'-imidazolyl-urea.

The Example which follows shows the biological action of the novel compounds.

EXAMPLE A

Leaves of wheat seedlings, of the Jubilar variety, grown in pots are sprayed with an aqueous emulsion containing a mixture of 80% by weight of active ingredient and 20% by weight of emulsifier and after the spray coating has dried the leaves are dusted with oidia (spores) of powdery mildew of wheat (*Erysiphe graminis* var. tritici). The test plants are then placed in a greenhouse at from 20° to 22° C. and from 75 to 80% relative atmospheric humidity. The degree of development of the mildew is assessed after 10 days.

| Active ingredient No. | Infection of the leaves after spraying with a X % strength liquor of active ingredient | | |
|---|---|---|---|
| | X = 0.025 | X = 0.012 | X = 0.006 |
| 1 | 0 | 0 | 2 |
| 4 | 0 | 2–3 | 4 |
| 16 | 0 | 0 | 0 |
| 19 | 0 | 2 | 2 |
| 21 | 0 | 1 | 1 |
| 26 | 0 | 0 | 2 |
| 43 | 0 | 0 | 0 |
| 49 | 0 | 0 | 0 |
| 55 | 0 | 0 | 0 |
| Control (untreated) | 5 | | |

0 = no fungal innfection, graded up to 5 = total infection.

The compounds according to the invention are furthermore very suitable for the preparation of novel fungicides of the general formula V

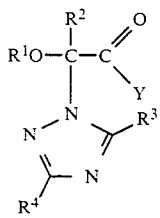

(V)

where $R^1$, $R^2$, $R^3$ and $R^4$ have the above meanings and Y is $OR^5$, $SR^5$ or

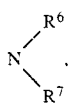

where $R^5$ is unsubstituted or substituted alkyl, alkenyl, alkynyl, cycloalkyl, cycloalkenyl, aryl, arylalkyl, heteroaryl, heteroarylalkyl or trialkylsilyl, $R^6$ is hydrogen or has one of the meanings given for $R^5$ and $R^7$ is hydrogen or, independently of $R^6$, has one of the meanings given for $R^5$ or is hydroxyl or is unsubstituted or halogen-substituted alkoxy or alkylthio or is cyano or cyanoalkyl or is $NR^8R^9$, where $R^8$ and $R^9$ independently of one another are hydrogen or unsubstituted or substituted alkyl or aryl, or $R^6$ and $R^7$ together with the adjoining nitrogen are an unsubstituted or substituted ring system which may or may not contain one or more double bonds and/or may additionally be interrupted by one or more hetero-atoms, eg. oxygen, nitrogen or sulfur.

A compound of the formula V is obtained, for example, by first reacting a compound of the formula I with N,N'-carbonyldiimidazole in tetrahydrofuran and then adding a compound of the formula VI

HY    (VI)

where Y has the above meanings.

Some of the compounds V have a systemic action and may be employed as leaf fungicides and soil fungicides. For example, they are distinctly superior to t-butyl 2-phenyl-(1',2',4'-triazol-1'-yl)-acetate, disclosed in German Laid-Open Application DOS No. 2,638,470, in combating, in particular, mildew and rust fungi.

USE EXAMPLES (a) 16 parts of diethyl sulfate are added to 13.6 parts of diazabicyclononene and 29 parts of 2-(2',4'-dichlorophenoxy)-2-(1',2',4'-triazol-1'-yl)-acetic acid in 150 parts of acetone, whilst cooling with ice and stirring, and stirring is continued overnight at room temperature. The mixture is then concentrated, the residue is taken up in methylene chloride and the extract is washed twice with water. After drying and concentrating, the residue is mixed with diisopropyl ether/petroleum ether and the resulting precipitate is filtered off. After drying, 27 parts (85% of theory) of ethyl 2-(2',4'-dichlorophenoxy)-2-(1',2', 4'-triazol-1'-yl)-acetate of melting point 167°–168° C. are obtained.

(b) 13 parts of N,N'-carbonyldiimidazole are added to 23.3 parts of 2-(4'-phenylphenoxy)-2-(1',2',4'-triazol-1'-yl)-acetic acid in 150 parts of tetrahydrofuran and the mixture is stirred at room temperature until the evolution of $CO_2$ has ceased. 6 parts of tert.-butanol are then added and the reaction mixture is stirred overnight at room temperature. It is then poured into 1,000 parts of ice water and the precipitate is filtered off. After drying, 21.3 parts (76% of theory) of tert.-butyl 2-(4'-phenylphenoxy)-2-(1',2',4'-triazol-1'-yl)-acetate of melting point 108°–110° C. are obtained.

We claim:

1. A one step process for the preparation of a 1,2,4-triazole derivative of the formula I

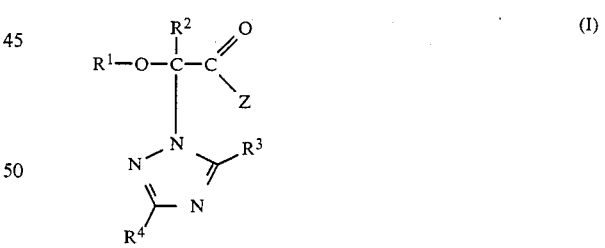

(I)

where
$R^1$ is unsubstituted phenyl or phenyl substituted by halogen or trifluoromethyl, $R^2$ is hydrogen or methyl, $R^3$ and $R^4$ are each hydrogen and Z is hydroxy, which process comprises:

reacting a compound of the formula II

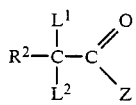

(II)

where $R^2$ and Z have the above meanings and $L^1$ and $L^2$ are nucleophilically displaceable leaving groups, with a hydroxy compound of the formula III
$$R^1-OH \quad \text{(III)}$$
where $R^1$ has the above meaning, or a salt thereof, and with a 1,2,4-triazole of the formula IV
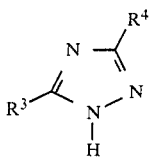
where $R^3$ and $R^4$ have the above meanings, or a salt thereof, in the presence or absence of a solvent or diluent and/or an acid acceptor and in the presence or absence of a reaction accelerator.
* * * * *